United States Patent [19]

Lambert

[11] 4,410,455

[45] Oct. 18, 1983

[54] PROCESS FOR PRODUCING A HYDROGENATION CATALYST

[75] Inventor: Peter J. Lambert, Billingham, England

[73] Assignee: Imperial Chemical Industries PLC, London, England

[21] Appl. No.: 306,346

[22] Filed: Sep. 28, 1981

[30] Foreign Application Priority Data

Oct. 22, 1980 [GB] United Kingdom ................ 8033987

[51] Int. Cl.³ ..................... B01J 21/04; B01J 23/44; B01J 23/58
[52] U.S. Cl. .................................... 502/327; 585/260

[58] Field of Search .................................. 252/466 PT

[56] References Cited

U.S. PATENT DOCUMENTS 3,218,268 11/1965 Arnold .......................... 252/466 Pt
4,126,645 11/1978 Collins .............................. 585/260

*Primary Examiner*—W. J. Shine
*Attorney, Agent, or Firm*—Cushman, Darby & Cushman

[57] ABSTRACT

Hydrogenation catalyst production by calcining a calcium aluminate cement catalyst support at 900°-1050° C. followed by impregnation with a palladium salt solution of pH below 1.3.

6 Claims, No Drawings

PROCESS FOR PRODUCING A HYDROGENATION CATALYST

This invention relates to a method of making a material suitable for use as a catalyst for the selective hydrogenation of highly unsaturated hydrocarbons in the presence of less unsaturated hydrocarbons.

The manufacture of unsaturated hydrocarbons usually involves cracking saturated and/or higher hydrocarbons and produces a crude product containing, as impurities, hydrocarbons that are more unsaturated than the desired product but which are very difficult to separate by fractionation. The commonest example is ethylene manufacture in which acetylene is a contaminant. In a similar way, the formation of propylene is accompanied by hydrocarbons of the empirical formula $C_3H_4$ (methyl acetylene and/or allene), and the formation of butadiene by vinyl acetylene. Such highly unsaturated hydrocarbons can be removed by hydrogenation using process conditions and a carefully formulated catalyst such that no significant hydrogenation of the desired hydrocarbon takes place.

Two general types of gaseous selective hydrogenation processes for purifying unsaturated hydrocarbons have come into use. One, known as "front-end" hydrogenation, involves passing the crude gas from the initial cracking step, after removal of steam and condensible organic matter, over a hydrogenation catalyst. The crude gas normally contains a relatively large amount of hydrogen, far in excess of that required to hydrogenate the acetylenes and sufficient in fact to hydrogenate a substantial part of the olefin present. Despite this hydrogen excess, operation with sufficient selectivity to give olefins of polymerisation quality is well established and catalyst lives of many years are obtained. In the other type, known as "tail-end" hydrogenation, the crude gas is fractionated and the resulting product streams are reacted with hydrogen in slight excess over the quantity required for hydrogenation of the highly unsaturated hydrocarbons present. The tail-end hydrogenation is less critical than front-end hydrogenation in that at the low hydrogen excess a runaway reaction is not possible; however, there is a greater tendency to deactivation of the catalyst and formation of polymers from the highly unsaturated hydrocarbons may occur as an alternative to the hydrogenation thereof. Consequently periodic regeneration of the catalyst is required.

Catalysts that have been found to be suitable for such selective hydrogenation reactions include palladium supported on certain alumina substrates, see for example UK Pat. No. 916,056 and U.S. Pat. No. 4,126,645. The catalyst is normally employed in the form of shaped pieces such as pellets, e.g. small cylindrical particles: heretofore pellets of about 3 mm diameter and 3 mm height have been used. Such shaped pieces are made by shaping, e.g. pelletising, a suitable catalyst support composition: the resultant shaped pieces are then converted to the desired support form by calcining, e.g. at temperatures in the range 1000° C. to 1200° C. The calcining temperature affects the physical properties of the catalyst support, notably its porosity and surface area. After calcining the palladium is deposited on the support by, for example, dipping or spraying.

One disadvantage of the alumina substrates (other than those of α-alumina) is that they often have poor strength and may tend to crumble. A further disadvantage of the alumina (including α-alumina) catalyst supports is that the precursors thereto tend to be difficult to fabricate, e.g. pelletise, into the desired shaped pieces.

In U.S. Pat. No. 4,239,530 there are described selective hydrogenation catalysts formed from a support composition containing a calcium aluminate cement and having a calcium:aluminium atomic ratio of between 1:4 and 1:10. This support composition is easier to fabricate than alumina and gives catalyst pieces that are of similar strength to those made from α-alumina and stronger than pieces formed from other grades of alumina.

After forming the support composition into the desired shaped pieces they are calcined and then palladium is applied to the calcined support.

While the palladium may be applied by a dry procedure such as sputtering, a catalyst precursor is preferably formed by a wet process by applying a solution of a palladium compound, for example a salt such as the chloride or nitrate, to the calcined catalyst support pieces e.g. by dipping or spraying, followed by drying. The resultant catalyst precursor is subsequently converted to the active catalyst by reducing the palladium compound to the active metal as described hereinafter.

For good selectivity the palladium should be present essentially only at or near the surface of the catalyst pieces. Thus the average depth of penetration of the palladium into the catalyst pieces should be less than 300 μm, preferably below 210 μm.

The depth of penetration may be determined by cutting a catalyst piece which has previously been reduced by dipping in a hydrazine solution and observing the extent of the darker palladium containing region.

Where a 'wet' process is employed for the incorporation of the palladium compound, the degree of penetration depends on a number of factors, e.g. the pore volume of the calcined support, the pH of the solution of the palladium compound, and the alkalinity of the calcined support. Where the calcining temperature is relatively high, e.g. 1100° C. or more, the desired penetration can be achieved by using a palladium compound, e.g. nitrate, solution having a pH of between about 1.7 and 1.9. However palladium nitrate solutions in this pH range are unstable and so this technique is not satisfactory for full scale operation, the use of solutions of lower pH, below 1.3, being desirable. The desired degree of penetration with solutions of pH below about 1.3 can be achieved by treatment of the calcined catalyst support pieces by dipping in an alkaline solution, e.g. aqueous solutions of hydroxides or carbonates of potassium or sodium, followed by drying, prior to dipping in the palladium salt solution. Such an alkali dip prior to calcining does not, however, give the desired control on the depth of palladium penetration.

It has now been found that if lower calcining temperatures are employed, the desired degree of penetration can be achieved with palladium solutions of pH below 1.3 without the need for an alkaline pretreatment. It is thought that the use of such lower calcining temperatures results in the calcium oxide in the cement being less strongly bound and so renders the support more alkaline. Indeed the desired penetration can be achieved using palladium solutions of pH below 1.0.

Accordingly the present invention provides a process for the manufacture of a precursor to a material suitable for use as a catalyst for the selective hydrogenation of highly unsaturated hydrocarbons in the presence of less unsaturated hydrocarbons comprising forming shaped pieces from a composition containing a calcium aluminate cement, said composition having a calcium- :aluminium atomic ratio within the range 1:4 to 1:10, calcining said shaped pieces at a temperature in the range 900° to 1050° C., and applying an aqueous solution of a reducible palladium compound having a pH below 1.3 to said calcined shaped pieces.

The present invetion also provides a process for the manufacture of a material suitable for use as a catalyst for the selective hydrogenation of highly unsaturated hydrocarbons in the presence of less unsaturated hydrocarbons comprising heating a precursor obtained by the above process to decompose the palladium compound to the active metal.

The calcining temperature is preferably within the range 930° to 1020° C.

By the term calcium aluminate cement we include those hydraulic cements containing one or more calcium aluminate compounds of the formula $nCaO.mAl_2O_3$ where n and m are integers. Examples of such calcium aluminate compounds include calcium monoaluminate ($CaO.Al_2O_3$), tricalcium aluminate ($3CaO.Al_2O_3$), penta calcium trialuminate ($5CaO.3Al_2O_3$), tricalcium penta aluminate ($3CaO.5Al_2O_3$), and dodeca calcium hepta aluminate ($12CaO.7Al_2O_3$). Some calcium aluminate cements, e.g. the so-called "high alumina" cements, may contain alumina in admixture with, dissolved in, or combined with, such calcium aluminate compounds. For example, a well known commercial high alumina cement has a composition corresponding to about 18% calcium oxide, 79% alumina and 3% water and other oxides. This material has a calcium:aluminium atomic ratio of about 1:5, i.e. $2CaO.5Al_2O_3$.

The support composition employed in the present invention has a calcium:aluminium atomic ratio within the range 1:4 to 1:10, preferably 1:5 to 1:8. Where the calcium aluminate cement is a "high alumina" cement, no additional alumina may be necessary but, in general, the support is made from the calcium aluminate cement to which an additional amount of alumina, conveniently in the form of the trihydrate, has been added.

Hence the support will usually be a refractory composition consisting of a calcined mixture of alumina and one or more of said calcium aluminate compounds.

The refractory composition should be relatively free of silica or silicates: preferably the silicon content is below 3% by weight of the composition.

The catalyst support pieces may be made by forming a calcium aluminate cement, with additional alumina as necessary, into the desired shape and subsequently calcining the shaped pieces.

Fabrication aids, such as graphite, may be incorporated into the composition prior to fabrication: typically the proportion of graphite is 1 to 5% particularly 2 to 4%, by weight of the composition.

To accelerate setting, a small amount of lime, e.g. up to 2% by weight of the composition, may also be incorporated into the fabrication composition.

A typical composition suitable for pellet formation comprises 50 to 70% by weight of a calcium aluminate cement (comprising 75 to 85% by weight of alumina and 15 to 25% by weight of lime) mixed with 24 to 48% by weight of alumina trihydrate, 0 to 2% by weight of lime, and 2 to 4% by weight of graphite.

We have found that the use of the calcium aluminate cement reduces considerably the pressure required to form catalyst support pieces of comparable strength to catalyst support pieces formed from alumina. This results in less wear and breakage of the pelletising machinery, e.g. punches and dies, and hence fabrication costs are reduced.

The catalyst conveniently is of the fixed-bed type, that is, in the form of shaped pieces whose largest dimension is in the range 2 to 12 mm and whose shortest dimension is at least one third of their largest dimension. Cylindrical compressed pellets or extrusions or approximate spheres are very suitable. Shaped pieces such as extrusions or pellets are especially preferred because they can be cheaply and readily made. A useful alternative catalyst support is in the form of a honeycomb, the specified calcium aluminate material forming the whole of the honeycomb or, less preferably, a coating on the surface of a honeycomb made from another material. Where the specified calcium aluminate material is present as a coating (secondary support) on another material (primary support), the primary support should be one that will not cause undesirable reaction of the hydrocarbons or else should be coated thickly and coherently enough to prevent access by the hydrocarbons. Preferably the palladium is present only in the secondary support. In view of the advantages conferred by the use of the calcium aluminate material, viz ease of fabrication and strength, it is preferred that the whole of the catalyst support is made from the calcium aluminate material.

Prior to calcining, the catalyst support pieces may be subjected to a water soaking step, followed by drying, to increase their strength. Preferably they are soaked in water for at least 12 hours and then dried, preferably at 100° to 150° C. Prior to such a soaking step, the catalyst support pieces may be fired at temperatures between 400° and 500° C., preferably for at least 2 hours.

As is known in the art, the calcining conditions affect the surface area and pore size of the catalyst support pieces. The calcining conditions are preferably such that the calcined catalyst support, before incorporation of the palladium has a pore volume of at least 0.2 $cm^3g^{-1}$ and a surface area of between 15 and 35 $m^2g^{-1}$.

The pore volume is defined as the difference between the reciprocal of the "mercury" density and the reciprocal of the "helium" density of the sample. These densities, and the surface area, are determined by the following methods which are applied to samples which have been dried in air at 110° C.:

1. Mercury density. The density of the catalyst immersed in mercury at 20° C. and 900 mm Hg pressure is determined after allowing 15 minutes for the system to equilibrate. This measurement represents the density of the solid containing pores not penetrated by mercury, i.e. pores of radius small than about $6 \times 10^4$ Å.
2. Helium density. The density of the catalyst immersed in helium at room temperature is determined: this represents the true density of the ultimate solid material.
3. Surface area. This is determined, after degassing the sample in flowing nitrogen for 40 minutes at 150° C., by the method of Brunauer, Emmett, and Teller (JACS 60 309 (1938)) by measuring the quantity of nitrogen absorbed on the catalyst at the boiling point of liquid nitrogen; in calculating the surface area, the cross sectional area of the nitrogen molecule is taken as 16.2 square Angstrom units.

It has been found that generally the surface area increases on incorporation of the palladium. It is thought that this increase in surface area results from some rehydration of the catalyst support during palladium incorporation followed by the formation of alternative crystalline forms upon reheating. The surface area of the catalyst pieces, i.e. after incorporation of the palladium is preferably less than 50 $m^2g^{-1}$.

The activity and selectivity of the catalyst depends on the amount of palladium incorporated, its distribution within the catalyst support, and its physical form. The overall palladium content of the catalyst pieces is preferably in the range 0.02 to 0.06% by weight.

Throughout the palladium containing region of the catalyst pieces the palladium content should be at least 0.005% by weight while the average palladium content of this palladium containing region should be 0.05 to 2% by weight. At depths greater than the palladium containing region, small amounts, less than 0.005% by weight, of palladium may be present.

As mentioned hereinbefore, after application of the palladium compound to the shaped pieces, they are dried, for example at a temperature within the range 25° C. to 150° C., conveniently at about 100° C. and the catalyst precursor may, with or without a distinct drying step, be heated to decompose the palladium compound, suitably at a temperature up to 500° C., especially in the range 150° C. to 450° C. The catalyst precursor pieces may be treated with hydrogen to complete reduction to palladium metal, for example during the heating step just mentioned and/or during an additional heating step (in which case the temperature should be in the range 25° to 450° C.) after the first heating step but before use. If there is no preliminary reduction step, the reduction of the catalyst precursor to the active catalyst may be effected when it is first used in the selective hydrogenation process. If the catalyst is reduced before use it may be stored under an inert atmosphere but should preferably not be kept for prolonged periods in hydrogen.

The palladium metal in the active catalyst is preferably in the form of crystallites having a size of less than 40 Å. The crystallite sizes may be determined by electron microscopy. If the crystallite size is above 40 Å, the catalyst becomes less selective.

When using relatively small catalyst support pieces, e.g. cylinders approximately 3 mm diameter and 3 mm length, a palladium crystallite size below 40 Å may be readily achieved when the palladium compound is applied by dipping. However dipping larger pieces e.g. 5.4 mm diameter and 3.6 mm length results in larger palladium crystallites. With such larger pieces, a spraying technique enables the water uptake (which affects the crystallite size) to be reduced giving crystallites below 40 Å.

Spraying is thus a preferred method of application of the palladium compound and this technique also allows the desired uptake and penetration of palladium to be more carefully controlled. The catalysts made in accordance with the present invention are of use for the selective hydrogenation of highly unsaturated hydrocarbons in the presence of less unsaturated hydrocarbons.

When the process is a "front-end" hydrogenation, the temperature is suitably up to 250° C., for example 60° to 150° C.; the pressure is suitably in the range 1 to 70, for example 8 to 40, atmospheres absolute; and the space velocity is suitably in the range 100–20,000 for example 5000–15,000 $hour^{-1}$, that is, liters of gas per liter of catalyst filled space per hour, calculated for 20° C., 1 atmosphere absolute pressure. The volume percentage composition of the gas fed to the catalyst is suitably as follows for a process producing ethylene and/or propylene as main products:

ethylene or propylene: 10 to 45 or each up to 20 when both are present
higher hydrocarbons: up to 2
acetylene and/or $C_3H_4$: 0.01 to 2
hydrogen: 5 to 40
unreactive gases (alkanes, nitrogen): balance For long catalyst life without regeneration, the hydrogen content is preferably at least 5 times by volume as much as the content of acetylene and $C_3H_4$.

When the process is a "tail-end" hydrogenation the temperature is suitably in the range 40°–150° C.; the pressure is suitably in the range 1–70, for example, 8–40 atmospheres absolute; and the space velocity is suitably in the range 500–7000 $hour^{-1}$. The hydrogen content should be at least sufficient to hydrogenate to mono-olefin all the highly unsaturated hydrocarbons present and is preferably 1.5 to 3 times that content for acetylene and 1.1 to 3 times that content for $C_3H_4$. The life of the catalyst between regenerations is longer the higher the hydrogen content of the gas, but this advantage is counter balanced by the expense of separating and recycling greater quantities of saturated hydrocarbon. The gas passed over the catalyst typically contains up to about 6% (for example 0.1 to 3) of highly unsaturated hydrocarbons and at least 50%, commonly over 95% of the desired mono-olefin or conjugated diolefin.

When the process is a "tail-end" liquid-phase selective hydrogenation, the temperature is typically 0°–50° C., the pressure up to about 50 atmospheres absolute, and the space velocity typically 5–40 kg per hour per liter of catalyst filled space. The liquid hydrocarbon suitably trickles downwards over the catalyst in a substantially stationary hydrogen atmosphere.

Whichever type of hydrogenation is used, it appears to be advantageous to have a small quantity of carbon monoxide present. In a front-end hydrogenation the proportion of carbon monoxide is suitably 0.03 to 3% by volume of the total gas mixture. Such a content commonly enters in as a by-product of the initial cracking reaction. In a tail-end hydrogenation the proportion is suitably in the range 4 to 500 ppm by volume; it may be added deliberately if fractionation of the crude gas has removed it or left too little of it.

The invention is illustrated by the following examples.

EXAMPLE 1

Preparation of catalyst support 600 g of a calcium aluminate cement containing 79% by weight of alumina and 18% by weight of lime, 396 g of alumina trihydrate, 10 g of lime, and 36 g of graphite were mixed and then fabricated, using a pelletiser, into cylindrical pellets of 3.2 mm diameter and 3.2 mm height. These raw pellets had a bulk density of 1.54 g $cm^{-3}$ and a vertical crushing strength of about 50 kg. (The vertical crushing strength is the compression load in the direction of the cylinder axis of a pellet that has to be applied to cause the pellet to break). By way of comparison to achieve a raw alumina pellet of similar strength, a considerably higher load, 40–60% greater, was required on the pelletising machinery. The use of such higher loads reduces the life of the punches and dies employed.

The raw pellets were then fired for 4 hours at 450° C. and then soaked in water for 16 hours. They were then dried for 5 hours at 120° C. The dried pellets then had a vertical crushing strength of 100 kg. The dried pellets were then calcined for 6 hours at 1000° C. whereupon they gave pellets having a water absorption of 25% by weight and a vertical crushing strength of about 70 kg. By way of comparison standard calcined alumina supported selective hydrogenation catalyst pellets had a vertical crushing strength of only 23 kg.

The catalyst support pieces had the following characteristics:
surface area: 24.2 m$^2$g$^{-1}$
helium density: 3.25 g cm$^{-3}$
mercury density: 1.81 g cm$^{-3}$
pore volume: 0.24 cm$^3$g$^{-1}$
pore radius: 200 Å
(The pore radius, assuming the pores are cylindrical and of the same size, is twice the pore volume divided by the surface area).

Impregnation of the catalyst support

The calcined pellets were impregnated with palladium by dipping 35.5 g of the pellets for 2 minutes in 100 ml of an aqueous solution of pH 0.98, containing 1.5 ml of a 10% by weight palladium nitrate solution. The impregnated pellets were dried for 6 hours at 450° C. which also served to decompose the palladium nitrate.

The overall palladium content was 0.049% by weight while the extent of the palladium containing region, (i.e. the penetration) was 100 μm. The surface area of the impregnated catalyst was 35.2 m$^2$g$^{-1}$.

Use of the catalyst

The activity of the catalyst was assessed by using it for the laboratory selective hydrogenation of a gas stream containing:
15% v/v hydrogen
35% v/v ethylene
0.1% v/v acetylene
0.1% v/v carbon monoxide
balance nitrogen
The catalyst was first pretreated at 150° C. for 4 hours with a nitrogen gas stream containing 5% by volume hydrogen, and then used for the hydrogenation reaction at a space velocity of 10,000 hr$^{-1}$ at various temperatures.

The activity and selectivity of the catalyst at each temperature was assessed by measuring the acetylene and ethane contents of the exit gas. The activity is the ratio of the exit and inlet acetylene contents while the ethane content gives an indication of the selectivity.

By way of comparison a commercially available alumina supported palladium selective hydrogenation catalyst (ICI Hydrogenation catalyst 38-1) was tested under the same conditions. The catalyst made according to the present invention had superior activity and selectivity to the commercially available hydrogenation catalyst.

EXAMPLE 2

Similar results were obtained when Example 1 was repeated but using an impregnation solution of pH 0.78. The penetration was 182 μm, the overall palladium content was 0.046%, and the surface area of the impregnated catalyst was 37.1 m$^2$g$^{-1}$.

EXAMPLE 3

Example 1 was repeated but employing a calcining temperature of about 940°-950° C. and a palladium nitrate solution of pH 1.06. The surface area of the calcined support, before impregnation, was 27 m$^2$g$^{-1}$.

EXAMPLE 4

Example 1 was repeated but using a calcining temperature of 980° C. and applying the palladium by spraying with a palladium nitrate solution of pH 1.03. The surface area of the calcined support, before impregnation, was 17.2 m$^2$g$^{-1}$.

EXAMPLES 5-8 (COMPARATIVE)

A catalyst support was made as in Example 1 but was calcined at 1100° C. The support had the following characteristics:
Surface area: 6.4 m$^2$g$^{-1}$
helium density: 3.2 g cm$^{-3}$
mercury density: 1.72 g cm$^{-3}$
pore volume: 0.27 cm$^3$g$^{-1}$
pore radius: 844 Å.
The calcined support pieces were impregnated and tested as in Example 1, but using impregnating solutions of various pH values and containing 1.7 ml of the 10% palladium nitrate solution. The results are shown in Table 1.

EXAMPLE 9 (COMPARATIVE)

Example 5 was repeated except that the impregnating solution had a pH of about 1.1-1.2 and the calcined support was dipped for 2 minutes in an aqueous sodium hydroxide solution containing 15 g l$^{-1}$ of NaOH, allowed to drain for 20 minutes and dried at 125° C. before impregnating with the palladium nitrate solution. The results are shown in Table 1.

EXAMPLE 10 (COMPARATIVE)

Example 9 was repeated except that the sodium hydroxide solution contained 30 g l$^{-1}$ NaOH. The results are shown in Table 1.

EXAMPLE 11 (COMPARATIVE)

Example 10 was repeated except that the treatment with the sodium hydroxide solution was effected before calcining. The results are shown in Table 1.

In Table 1 the activity (A) and selectivity (S) are compared with the alumina supported catalyst 38-1.
In the Table:
+ indicates that the property is superior to that of the alumina supported catalyst,
− indicates that the property is inferior to that of the alumina supported catalyst,
= indicates that the property is similar to that of the alumina supported catalyst.

TABLE 1

| Example | Calcining Temperature °C. | Impregnating Solution pH | Overall Pd content % by weight | Pd penetration μm | Surface Area m$^2$g$^{-1}$ | A | S |
|---|---|---|---|---|---|---|---|
| 1 | 1000 | 0.98 | 0.049 | 100 | 35.2 | + | + |
| 2 | 1000 | 0.78 | 0.046 | 182 | 37.1 | + | + |
| 3 | 940-950 | 1.06 | 0.048 | 94 | 42 | + | + |
| 4 | 980 | 1.03 | 0.05 | 92 | 48 | + | = |
| 5 | 1100 | 0.9 | 0.048 | 863 | 35.7 | − | − |
| 6 | 1100 | 1.4 | 0.036 | 295 | 12.4 | − | − |
| 7 | 1100 | 1.7 | 0.031 | 224 | 11.5 | = | = |
| 8 | 1100 | 1.9 | 0.044 | 158 | 14.7 | + | + |
| 9* | 1100 | 1.1-1.2 | 0.033 | 107 | 24.7 | + | + |
| 10** | 1100 | 1.1-1.2 | 0.029 | 82 |  | = | + |

TABLE 1-continued

| Example | Calcining Temperature °C. | Impregnating Solution pH | Overall Pd content % by weight | Pd penetration μm | Surface Area m²g⁻¹ | A | S |
|---|---|---|---|---|---|---|---|
| 11*** | 1100 | 1.1–1.2 | 0.032 | 444 | 5.1 | — | — |

*treatment with 15 g l⁻¹ NaOH before impregnation
**treatment with 30 g l⁻¹ NaOH before impregnation
***treatment with 30 g l⁻¹ NaOH before calcining From the table it is seen that, if high calcination temperature, e.g. 1100° C., are used, satisfactory catalysts can be obtained (e.g. Example 8), if impregnating solutions of relatively high pH are employed. However such solutions have a poor stability: thus after a short period of time, e.g. 1–2 hours, the palladium tends to precipitate from these solutions as a hydroxide and hence the solutions are unsuitable for making catalysts on a large scale.

It is also seen, from Examples 9 and 10, that, by using an alkali dip, after calcining but before palladium impregnation, satisfactory catalysts can by obtained using low pH impregnating solutions. However such a process has the disadvantage that an additional processing step, i.e. the alkali dip, is required.

I claim:

1. A process for the manufacture of a precursor to a material suitable for use as a catalyst for the selective hydrogenation of highly unsaturated hydrocarbons in the presence of less unsaturated hydrocarbons comprising
   (i) forming shaped pieces from a composition containing a calcium aluminate cement, said composition having a calcium:aluminium atomic ratio within the range 1:4 to 1:10,
   (ii) calcining said shaped pieces at a temperature in the range 900° to 1050° C., and
   (iii) applying an aqueous solution of a reducible palladium compound having a pH below 1.3 to said calcined shaped pieces.

2. A process as claimed in claim 1 wherein the calcining temperature is within the range 930° to 1020° C.

3. A process as claimed in claim 1 wherein the solution of the palladium compound has a pH below 1.0.

4. A process as claimed in claim 1 wherein the palladium compound solution is applied to the calcined shaped pieces by spraying.

5. A process for the manufacture of a material suitable for use as a catalyst for the selective hydrogenation of highly unsaturated hydrocarbons in the presence of less unsaturated hydrocarbons comprising heating a precursor obtained by a process as claimed in claim 1 to decompose the palladium compound to the active metal.

6. In a process for the manufacture of a material, suitable for use as a catalyst for the selective hydrogenation of highly unsaturated hydrocarbons in the presence of less unsaturated hydrocarbons, in the form of shaped pieces of a support material containing a calcium aluminate cement and having a calcium:aluminium atomic ratio in the range 1:4 to 1:10 deposited to an average depth of less than 300 μm with palladium, comprising forming said shaped pieces of the calcium aluminate cement containing support matrerial, calcining said shaped pieces, impregnating said calcined shaped pieces with an aqueous solution of a reducible palladium compound having a pH below 1.3 and heating the impregnated calcined shaped pieces to reduce the palladium compound to palladium metal, the improvement of performing said calcining step at a temperature in the range 900° to 1050° C.

* * * * *